United States Patent [19]

Cahoy

[11] 4,331,815

[45] May 25, 1982

[54] PROCESS FOR MANUFACTURING N-BENZYL-N-ISOPROPYL AMIDES

[75] Inventor: Roger P. Cahoy, Overland Park, Kans.

[73] Assignee: Gulf Oil Corporation, Pittsburgh, Pa.

[21] Appl. No.: 191,809

[22] Filed: Sep. 26, 1980

[51] Int. Cl.³ .................. C07C 103/34; C07C 103/76
[52] U.S. Cl. .................................. 564/142; 564/143; 564/176; 564/185; 564/219; 71/118
[58] Field of Search ................................ 564/142, 143

[56] References Cited

U.S. PATENT DOCUMENTS 3,852,350  12/1974  Wilson, Jr. .......................... 564/142
3,914,302  10/1975  Chan et al. ......................... 564/143
3,974,219   8/1976  Yamazaki et al. ................... 564/141

*Primary Examiner*—Jacqueline V. Howard
*Attorney, Agent, or Firm*—Deane E. Keith; Forrest D. Stine; Carl A. Cline

[57] ABSTRACT

In the manufacture of an N-benzyl-N-isopropyl amide by reaction of N-benzyl-N-isopropylamine with an acid chloride, the amide product is obtained in better purity and yield by employing excess benzylisopropylamine as the acid accepting agent and recovering the amine for re-use by reacting the amine hydrochloride by-product with aqueous sodium hydroxide.

8 Claims, No Drawings

PROCESS FOR MANUFACTURING N-BENZYL-N-ISOPROPYL AMIDES

DESCRIPTION OF THE INVENTION

In the manufacture of amides by reaction of an acid chloride with an amine, it is often the amine which is more expensive and an effort is made to utilize the amine completely. To accomplish this end, the acid chloride is often reacted with a molar equivalent amount of the amine in the presence of at least one molar equivalent amount of a tertiary amine, usually triethylamine. Usually a generous amount of a non-reactive organic solvent is included in the reaction mixture so as to facilitate thorough reaction and heat exchange during the exothermic amidation reaction. In U.S. Pat. No. 3,974,218 there is disclosed a process of this type for manufacturing certain N-benzyl-N-isopropylamides. The yields disclosed are between 60 and 90 percent. The method is one that consumes triethylamine because of recovery losses, besides failing to give near quantitative yields. Although the method is quite satisfactory for experimental purposes, when operated on a commercial scale it leaves something to be desired.

The present invention is an improved process for manufacturing N-benzyl-N-isopropyl amides by reaction of an acid chloride with benzylisopropylamine in which the product is obtained in both high purity and excellent yields.

Briefly, the improved process comprises the steps:

(a) Reacting two molar equivalents of benzylisopropylamine with each mole of acid chloride in a nonreactive organic solvent medium at a temperature within the range of 5° to 100° C.;

(b) Mixing water with the reaction product mixture to obtain an aqueous liquid phase and an organic liquid phase and separating the two phases;

(c) Washing the organic phase from step (b) with dilute sodium hydroxide, then with water;

(d) Distilling the washed organic phase, thereby removing water and non-reactive organic solvent, to yield the N-benzyl-N-isopropyl amide as distillation residue;

(e) Reacting the aqueous phase from step (b) with aqueous sodium hydroxide to yield a mixture consisting of an aqueous liquid phase and a liquid organic phase of lower specific gravity which consists essentially of benzylisopropylamine, and (f) Separating and recycling the benzylisopropylamine phase from step (e) to step (a).

The mixture consisting of non-reactive organic solvent, such as toluene, for example, in combination with the amide product possesses an enhanced solvent ability which holds the amine hydrochloride in solution and reduces viscosity of the reaction mixture during the exothermic amidation reaction. This effect is fortuitous, as it facilitates stirring and heat exchange. Furthermore, when the free amine is released by reaction of amine hydrochloride with sodium hydroxide, the low water solubility of benzylisopropylamine facilitates efficient separation and recovery. Recovery of amine is about 98 percent and the amine is recycled in about 95 to 96 percent purity (by weight). The operation of the process is illustrated by the following specific example. All quantities which are specified as parts are parts by weight.

EXAMPLE

Preparation of N-benzyl-N-isopropylpivalamide

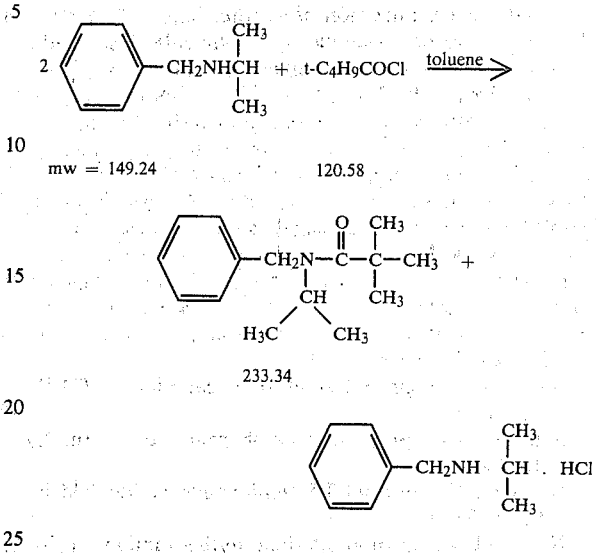

A properly equipped reaction vessel was purged with nitrogen and charged with 5.5 parts of dry toluene and 2.6 parts of N-benzyl-N-isopropylamine. With good agitation and full cooling water on the jacket, controlled addition of 1.0 part of pivaloyl chloride was initiated. The addition rate was adjusted in order to maintain the reaction temperature at 85°–90° C. When the addition of pivaloyl chloride was completed, low pressure steam replaced the cooling water on the jacket. The reaction mixture was stirred at 90°–95° C. for 30 minutes. After cooling the reaction mixture to 70°–75° C., there was added 3.7 parts of water and 0.06 part of hydrochloric acid. After stirring, the phases were allowed to separate. The more dense aqueous phase indicated a pH of about 2. The 5.4 parts of aqueous phase were withdrawn and retained for N-benzyl-N-isopropylamine recovery. The organic reaction phase was stirred with 2.1 parts of 5% aqueous sodium hydroxide. The basic aqueous phase was withdrawn and discarded. The organic phase was washed with 2.1 parts of water. After phase separation, the aqueous phase was withdrawn and discarded.

Water was removed from the reaction solution by azeotropic distillation at atmospheric pressure. When the water removal was completed, the head temperature rose rapidly to 107°–109° C. The reaction solution was cooled to 50° C. and the remaining toluene was removed by reduced pressure distillation. At a vessel temperature of 115°–120° C. at 35 mm Hg of vacuum, the solvent removal was judged to be complete. There was obtained 5.2 parts of dry toluene for recycle purposes. The crude product (1.9 parts), $n_D26$ 1.5065, was subjected to chromatographic analysis. Found: 95.8 weight% N-benzyl-N-isopropylpivalamide and 0.8 weight% toluene.

The above described 5.4 parts of aqueous solution of N-benzyl-N-isopropylamine hydrochloride was placed in a reaction vessel. With good agitation and jacket cooling, there was added portionwise 0.77 part of aqueous 50% sodium hydroxide at which time the aqueous phase indicated pH 12. After phase separation, the more dense aqueous phase was withdrawn and discarded. The organic phase was dried by stirring with 0.77 part of aqueous 50% sodium hydroxide. After phase separation, the aqueous sodium hydroxide was withdrawn and retained for neutralization of another batch of aqueous N-benzyl-N-isopropylamine hydrochloride. The crude product (1.3 parts) was sampled for chromatographic analysis. Found: 95.7 weight% N-benzyl-N-isopropylamine. The latter was distilled through a simple fractionation column at 83°–85° C./8 mm Hg to yield 1.2 parts of purified amine. Found by analysis: 98.7% N-benzyl-N-isopropylamine. The recovered N-benzyl-N-isopropylamine was then recycled to the first reaction step of the process. The process as described and specifically exemplified has utility for the manufacture of other N-benzyl-N-isopropyl substituted alkanoic and aromatic amides which have demonstrated specific herbicidal efficacy. These include:

N-benzyl-N-isopropyl-3-chlorobenzamide (M.P. 62°–64° C.)
N-benzyl-N-isopropyl-3-bromobenzamide ($n_D25$ 1.5822)
N-benzyl-N-isopropyl-3,5-dichlorobenzamide (M.P. 96°–98° C.)
N-benzyl-N-isopropyl-3,5-dimethylbenzamide (viscous oil, $n_D27$ 1.5457)
N-benzyl-N-isopropyl-3,5-dimethoxybenzamide (viscous oil, $n_D24$ 1.5448)
N-benzyl-N-isopropyl-3,5-dibromobenzamide (M.P. 89°–90° C.)

I claim:

1. The process for manufacturing N-benzyl-N-isopropyl carboxamides comprising the steps:
   (a) Reacting two molar equivalents of benzylisopropylamine with each mole of carboxylic acid chloride in a non-reactive organic solvent medium at a temperature within the range of 5° to 100° C.;
   (b) Mixing water with the reaction product mixture to obtain an aqueous liquid phase and an organic liquid phase and separating the two phases;
   (c) washing the organic phase from step (b) with dilute sodium hydroxide, then with water;
   (d) Distilling the washed organic phase, thereby removing water and non-reactive organic solvent, to yield the N-benzyl-N-isopropyl amide as distillation residue;
   (e) Reacting the aqueous phase from step (b) with aqueous sodium hydroxide to yield a mixture consisting of an aqueous liquid phase and a liquid organic phase of lower specific gravity which consists essentially of benzylisopropylamine, and
   (f) Separating and recycling the benzylisopropylamine phase from step (e) to step (a).

2. The process of claim 1 wherein N-benzyl-N-isopropylpivalamide is the product of step (d).

3. The process of claim 1 wherein N-benzyl-N-isopropyl-3-chlorobenzamide is the product of step (d).

4. The process of claim 1 wherein N-benzyl-N-isopropyl-3-bromobenzamide is the product of step (d).

5. The process of claim 1 where N-benzyl-N-isopropyl-3,5-dichlorobenzamide is the product of step (d).

6. The process of claim 1 wherein N-benzyl-N-isopropyl-3,5-dimethylbenzamide is the product of step (d).

7. The process of claim 1 wherein N-benzyl-N-isopropyl-3,5-dimethoxybenzamide is the product of step (d).

8. The process of claim 1 wherein N-benzyl-N-isopropyl-3,5-dibromobenzamide is the product of step (d).

* * * * *